United States Patent
Roberts et al.

[11] Patent Number: 5,755,243
[45] Date of Patent: May 26, 1998

[54] DENTAL FLOSS WITH THERMOPLASTIC COATING

[75] Inventors: Michael Roberts, Braintree, Mass.; David Anglin, Santa Clara, Calif.; Brad Castillo, San Ramon, Calif.; Casper Chiang, Danville, Calif.; Jean Spencer, Boston, Mass.

[73] Assignee: Gillette Canada, Inc., Kirkland, Canada

[21] Appl. No.: 671,064

[22] Filed: Jun. 27, 1996

[51] Int. Cl.$^6$ ................................. A61C 15/00
[52] U.S. Cl. ............................................ 132/321
[58] Field of Search ....................... 132/321, 323, 132/329

[56] References Cited

U.S. PATENT DOCUMENTS

| | | | |
|---|---|---|---|
| 174,619 | 3/1876 | Clark . | |
| 660,943 | 10/1900 | Bauermeister . | |
| 2,667,443 | 1/1954 | Ashton . | |
| 2,700,636 | 1/1955 | Ashton . | |
| 2,748,781 | 6/1956 | Collat . | |
| 3,412,192 | 11/1968 | Clapson . | |
| 3,492,131 | 1/1970 | Schlatter . | |
| 3,615,671 | 10/1971 | Shoaf et al. . | |
| 3,642,491 | 2/1972 | Schlatter . | |
| 3,699,979 | 10/1972 | Muhler et al. . | |
| 3,771,536 | 11/1973 | Dragen . | |
| 3,789,858 | 2/1974 | Pesce . | |
| 3,800,046 | 3/1974 | Schlatter ........................ | 426/168 |
| 3,830,246 | 8/1974 | Gillings . | |
| 3,837,351 | 9/1974 | Thornton . | |
| 3,838,702 | 10/1974 | Standish et al. . | |
| 3,896,824 | 7/1975 | Thornton . | |
| 3,897,795 | 8/1975 | Engel . | |
| 3,943,949 | 3/1976 | Ashton et al. . | |
| 4,008,727 | 2/1977 | Thornton . | |
| 4,029,113 | 6/1977 | Guyton . | |
| 4,033,365 | 7/1977 | Klepak et al. . | |
| 4,071,615 | 1/1978 | Barth .............................. | 424/52 |
| 4,142,538 | 3/1979 | Thornton . | |
| 4,291,017 | 9/1981 | Beierle et al. .................. | 424/52 |
| 4,414,990 | 11/1983 | Yost . | |
| 4,548,219 | 10/1985 | Newman et al. ................ | 424/70 |
| 4,627,975 | 12/1986 | Lynch ............................. | 424/49 |
| 4,638,823 | 1/1987 | Newman et al. . | |
| 4,817,643 | 4/1989 | Olson ............................. | 132/329 |
| 4,911,927 | 3/1990 | Hill et al. ....................... | 424/443 |
| 4,952,392 | 8/1990 | Thame ........................... | 424/58 |
| 4,974,615 | 12/1990 | Doundoulakis ................. | 132/321 |
| 4,986,288 | 1/1991 | Kent et al. ..................... | 132/321 |
| 4,996,056 | 2/1991 | Blass ............................. | 424/443 |
| 4,998,978 | 3/1991 | Varum .......................... | 132/321 |
| 5,033,488 | 7/1991 | Curtis et al. ................... | 132/321 |
| 5,063,948 | 11/1991 | Lloyd ............................ | 132/321 |
| 5,284,169 | 2/1994 | Gilligan et al. ................ | 132/321 |
| 5,501,734 | 3/1996 | Oliphant ........................ | 118/234 |
| 5,505,216 | 4/1996 | Gilligan et al .................. | 132/321 |
| 5,526,831 | 6/1996 | Gilligan et al. ................ | 132/321 |
| 5,558,901 | 9/1996 | Gilligan et al. ................ | 132/321 |
| 5,633,286 | 5/1997 | Chen ............................. | 132/321 |

FOREIGN PATENT DOCUMENTS

| | | |
|---|---|---|
| 0 080 440 A1 | 6/1983 | European Pat. Off. . |
| 0 335 466 A2 | 10/1989 | European Pat. Off. . |
| 2 216 803 A | 10/1989 | United Kingdom . |

*Primary Examiner*—Cary E. O'Connor
*Attorney, Agent, or Firm*—Fish & Richardson P.C.

[57] ABSTRACT

Improved dental flosses are provided, including a fiber core, preferably a multifilament fiber, and an elastomeric outer layer.

56 Claims, 2 Drawing Sheets

DENTAL FLOSS WITH THERMOPLASTIC COATING

BACKGROUND OF THE INVENTION

Tooth decay and dental disease can be caused by bacterial action resulting from the formation of plaque about the teeth and/or the entrapment of food particles in interstices between the teeth. Removal of plaque and entrapped food particles reduces the incidence of caries, gingivitis, and mouth odors as well as generally improving oral hygiene. Conventional brushing has been found to be inadequate for removing all entrapped food particles and plaque. To supplement brushing, dental flosses and tapes have been recommended.

Dental flosses have been developed that include thickened "brush" portions and thin "floss" portions alternating along the length of the floss. The brush portion, when drawn between tooth surfaces, provides good cleaning action which removes materials left by a standard thin floss used alone.

To form a floss including brush portions, it is necessary to provide bulked filaments in a strand of floss, i.e., filaments which are separated and have a somewhat sinuous, random orientation.

Dental flosses, both in brush and thin floss form, often include additives such as flavors or colors. These flavors have been conventionally applied by coating the additive onto the surface of the floss. Some dental flosses and tapes have been coated with waxes to aid in insertion of the floss or tape between the teeth.

SUMMARY OF THE INVENTION

The present invention features improved dental flosses and filaments for use in manufacturing dental flosses.

The filaments include an inner core having relatively high tensile strength, and an outer sheath of a soft material. Preferably, the inner core is a conventional floss material, e.g., a multifilament fiber formed of a polymer selected from the group consisting of nylon, polyester, polypropylene and polyethylene. Other manmade or natural fibers may also be used. The outer sheath preferably includes a thermoplastic elastomer, and has a Shore A hardness of 10 or less. The outer sheath is preferably applied over the inner core as a coating, but alternatively the floss may be formed by other processes, e.g., by coextrusion, provided that the floss includes two or more components (sheath and core), and at least two of the components are present in the form of substantially separate phases having a distinct interface between them, rather than being intermixed. Preferred flosses include brush portions.

The invention further features methods of making the improved flosses. A preferred method includes (a) providing a multifilament fiber; and (b) applying a layer including a thermoplastic elastomer to the surface of the multifilament fiber. Preferred methods further include bulking the multifilament fiber prior to step (b), to form brush portions.

Additionally, the invention features methods of flossing the teeth of a mammal, e.g., a human, by inserting between two teeth of the mammal a length of a dental floss of the invention.

The term "dental floss", as used herein, is defined to include dental flosses, dental tapes, and similar articles, that are sized to be drawn between the teeth.

The term "brush portion", as used herein, refers to a portion of the dental floss that has been bulked to provide a segment of randomly distorted crinkled filaments with a yarn-like texture.

Other features and advantages of the invention will be apparent from the drawings, the following Detailed Description, and the claims.

DESCRIPTION OF THE PREFERRED EMBODIMENTS

Figure 1:
FIGS. 1 and 1a are photomicrographs of a dental floss according to the invention, at 50× and 117× magnification, respectively.

Preferred dental flosses of the invention include a core and an outer sheath of a soft polymer. Preferably, the core includes a multifilament fiber and the outer sheath includes a thermoplastic elastomer.

Preferred multifilament fibers include nylon, polyester, polypropylene and other polymers capable of imparting tensile strength and/or rigidity to the floss. Preferred fibers include bulked or "brush" sections, as described in U.S. Pat. Nos. 4,008,727, 4,277,297, 5,284,169 and 5,353,820, the disclosures of which are incorporated herein by reference. The fibers may be bulked using any desired process, with the sheath preferably being applied after bulking has taken place. Preferably, the brush sections, prior to application of the sheath layer, have a denier of from about 590 to 750 and include about 100 to 200 filaments.

Preferred TPEs (thermoplastic elastomers), include styrenic block copolymers, such as those available from Dexco Polymers, EniChem Elastomers, or, under the tradename KRATON, from Shell; polyether block amides such as those available under the tradename PEBAX from ELF Atochem; polyester elastomers such as those available under the tradename HYTREL from DUPONT; EVA (ethylene vinyl acetate); ethylene-propylene copolymers; low MFI polypropylene; and mixtures thereof. Styrenic block copolymers are particularly preferred, particularly triblock A-B-A copolymers in which A is a styrene unit and B is a butadiene, isoprene or ethylene-butylene unit. One preferred block copolymer of this type is a styrene-isoprene-styrene block copolymer with a styrene:isoprene ratio of 21:79, commercially available from Shell under the tradename KRATON D-1107. This copolymer has a Shore A hardness of 37, an elongation to break of 1300% and a 300% tensile modulus of only 345 kPa (50 psi). Other suitable thermoplastic elastomers include gelatinous thermoplastic elastomers, such as the gelatinous plasticized poly(styrene-ethylene-butylene-styrene) triblock copolymers disclosed in U.S. Pat. No. 5,262,468, the disclosure of which is incorporated herein by reference.

Preferably, the sheath layer also includes one or more extenders, to increase the softness of the sheath. Styrenic block copolymers may be extended with a wide variety of materials, as is well known in the art. Suitable extenders include oils, waxes, resins, asphalts, and other polymers (see, e.g., Technical Bulletin No. SC:1757-93, The Shell Chemical Company, describing extenders for KRATON block copolymers.) Extenders typically associate with either the styrene block or the rubber (isoprene, butadiene, etc.) block of styrenic block copolymers. Preferred extenders for increasing the softness of the polymer are those which associate with the rubber block. One preferred extender is mineral oil, e.g., DUOPRIME 90 mineral oil, commercially available from Lyondell Lubricants, a hydrocarbon petroleum oil which associates with the isoprene phase of KRATON D1107 block copolymer. Preferably, the sheath layer material includes a sufficient amount of extender to reduce the Shore A hardness of the material to zero or less. One preferred block copolymer/extender blend includes 32 parts KRATON D1107 block copolymer to 68 parts DUOPRIME 90 mineral oil.

The thermoplastic elastomer and extender are selected to provide a desired combination of softness and resistance of the sheath layer to tearing or abrasion when used.

If desired, the sheath layer may include other additives. For example, the sheath layer may contain an abrasive, for improved cleaning. Preferred abrasive/polymer combinations include nylon containing particles of kaolin, calcium carbonate, zinc oxide, silica, PTFE, or blends of these particles which are compatible. If desired, one or more additives may be absorbed or adsorbed on the surface of the abrasive particles, e.g., by drum drying, spray drying, fluidized bed processing, or other suitable methods as is known in the art. Also, the sheath layer may include a flavor oil such as peppermint oil (International Flavors and Fragrances Co.), pigments, e.g., titanium dioxide, to impart color to the floss, or antioxidants, to prevent discoloration.

Preferably, the coating level is from about 150% to 400%, more preferably about 200% to 260%, based on the denier of the fiber prior to and after coating with the sheath material. For example, preferred multifilament fibers have a denier of about 590 to 750 prior to coating, and a denier of from about 2200 to 2700 after coating with the sheath material. The optimum coating level will vary depending upon the material used as the sheath.

Figure 1A:

As shown in FIGS. 1 and 1a, in preferred brush flosses the sheath material is not only present on the surface of the fiber, but also is present between the filaments of the fiber.

Figure 2:
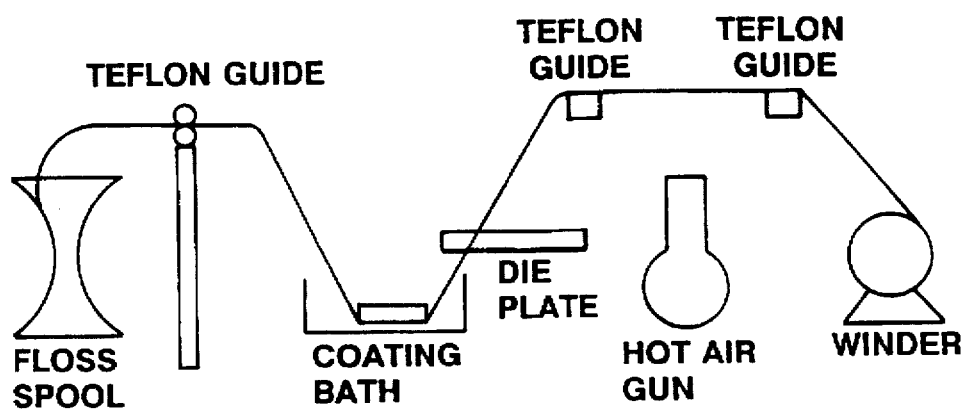
FIG. 2 is a schematic diagram showing a dental floss manufacturing process according to one embodiment of the invention.

One suitable method for applying the sheath layer is solution coating. A suitable solution coating process is shown schematically in FIG. 2. As shown, the multifilament fiber is guided under low tension from a spool through a bath of coating solution and upon exiting the bath passes through a die orifice. The size of the die orifice will determine the final coating level. The preferred coating levels discussed above are generally obtained by using die orifices having diameters of from about 0.038" to 0.042". After passing through the die orifice, the coated fiber passes into a hot air stream, provided by, e.g., a hot air gun or an oven, to drive the solvent from the coating solution and thus dry the coating. Preferred hot air temperatures are generally from about 60° to 150° C.; the preferred temperature is selected based on the evaporation properties of the solvent used in the coating solution. Finally, the floss is taken up on a motorized winder. Preferred speeds of travel of the fiber through the above process are from 1 to 100 meters/minute, with 40 to 100 meters/minute being preferred for commercial processing. The coated floss may, if desired, be placed in an oven at 60° to 150° C. overnight to remove any residual solvent.

The coating solution includes the thermoplastic elastomer, a solvent, and an extender if necessary. If KRATON block copolymers are used, suitable solvents or solvent blends are generally those having a solubility parameter of from about 7 to 10, more preferably 7.7 to 9.4. One preferred solvent is OXSOL 100 solvent, commercially available from Occidental Chemical Co. (CAS Number 98-56-6). While this solvent has a solubility parameter of only 7.3, it is desirable because it is safe and considered to be environmentally-friendly. Many other solvents may also be used. Preferred coating solutions contain from about 10 to 80% solvent. Generally, when 20% or less solvent is used, the coating solution will be in the form of a homogeneous gel which will flow upon application of mild heat (e.g., 30° to 50° C.). To prepare the coating solution, the components are mixed together and stirred, with mild heat (30° to 50° C.) being applied if necessary.

Figure 3:
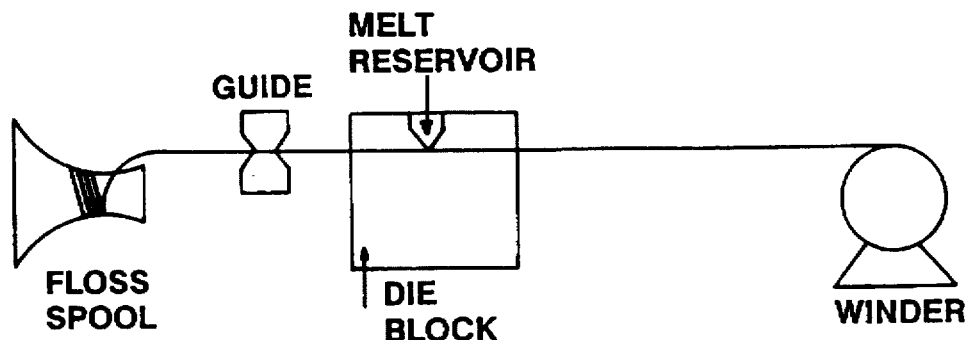
FIG. 3 is a schematic diagram showing a dental floss manufacturing process according to another embodiment of the invention.
Figure 3A:
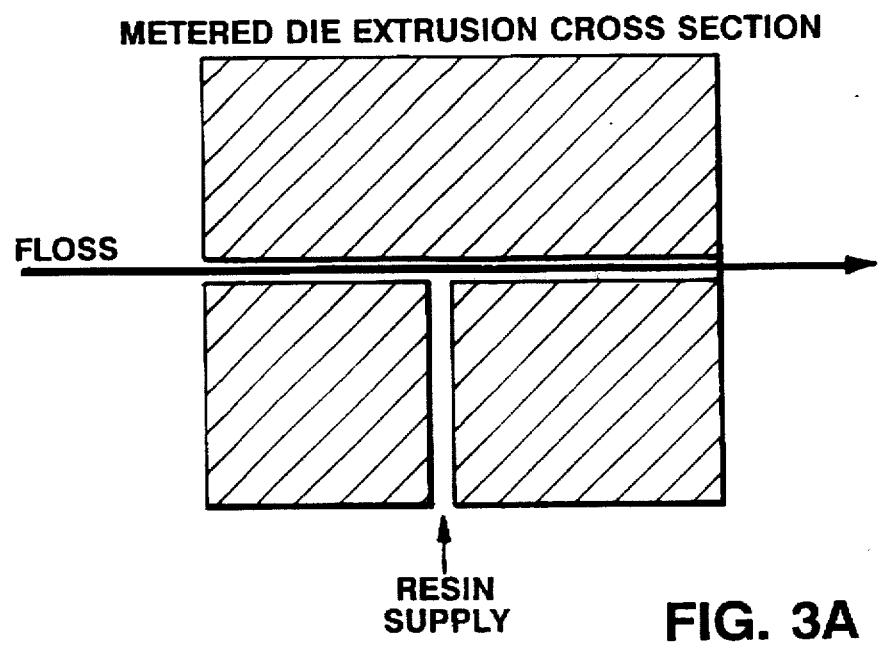
FIG. 3a is a schematic detail view of a metered die block used in the process of FIG. 3.

One alternative process for coating the multifilament fiber is shown in FIG. 3. In this process, the thermoplastic elastomer (with extender, if necessary) is applied as a hot melt, rather than as a solvent-based solution. As shown in FIG. 3, the multifilament fiber is first taken from a spool, pulled through a metered die block (FIG. 3a), into which the hot melt is pumped through a nipple connected to the resin supply inlet, and wound under low tension. At the outlet, the die area is preferably about 0.001 square inches (equal to a 0.035" diameter round orifice). A reservoir perpendicular to the orifice is filled with the coating material (elastomer or elastomer/extender blend). The die block is fitted with heater probes and a thermocouple. The heater is set at a temperature sufficient to melt the coating material, and a plunger rod is used to feed the melt into the orifice, thus coating the floss. On exiting the die, the floss cools and is subsequently wound up. Suitable temperatures for the die block can be determined empirically for a particular elastomer or elastomer/extender blend and multifilament fiber; a suitable melt temperature will cause the coating material to flow easily and, if the multifilament fiber is a brush floss, to have sufficiently low viscosity so that the bulking of the brush floss is not unacceptably reduced (excessively high viscosity may in some cases cause the bulked filaments to be compressed together). Suitable hot melt processing equipment is available from Nordson, Co., Duluth, Ga.

The following examples are intended to be illustrative and not limiting in nature.

Example 1

A coating solution was prepared with 360 grams OXSOL 100 solvent, 45 grams KRATON D1107 rubber, 95 grams DUOPRIME 90 mineral oil, and 5 grams peppermint oil. These ingredients were stirred together overnight to yield a homogeneous solution. ORAL-B ULTRAFLOSS® dental floss, having a denier of 750, was threaded through the processing line shown in FIG. 2. The die used had an orifice diameter of 0.042 inches. Approximately 200 grams of coating solution was poured into the coating bath, and the hot air gun was set to give a temperature of 60° C. around the floss. The coating process was started by setting the winder speed at 4 meters per minute. The coated floss was then removed from the winder and placed in an oven at 60° C. overnight. The final denier of the coated floss was 2524 (a coating level of 238% based on the initial denier of the ULTRAFLOSS dental floss).

Example 2

A block of extended elastomer was prepared for melt coating as follows. 35 grams KRATON D1107 rubber, 65 grams DUOPRIME 90 mineral oil, and 0.7 grams IRGANOX 1010 antioxidant were added to a 1 liter reactor. The mixture was heated to 135° C. and manually stirred with a glass rod periodically. A homogeneous melt was obtained after 30 minutes which was then cooled to room temperature and removed from the reactor as a solid block. The block was cut into strips and placed in the melt reservoir of the die block shown in FIG. 3. The temperature of the die block was set at 150° C. ORAL-B ULTRAFLOSS® dental floss was then threaded through the processing line shown in FIG. 3. Coated floss similar to that produced in Example 1 was produced by drawing the dental floss through the metered die block and allowing it to cool to room temperature.

Other embodiments are within the claims. For example, a wire coating die can be used to apply the thermoplastic elastomer to the multifilament fiber, using wire coating techniques that are well known in the coating art, e.g., using an extruder and a gear pump to extrude the elastomer through the wire coating die.

What is claimed is:

1. A dental floss comprising a fiber core and an outer sheath comprising a thermoplastic elastomer and an extender selected from the group consisting of oils, resins, and asphalts.

2. The dental floss of claim 1 wherein the fiber core comprises a multifilament fiber.

3. The dental floss of claim 2 wherein the multifilament fiber includes a brush portion.

4. The dental floss of claim 1 wherein the thermoplastic elastomer comprises a block copolymer.

5. The dental floss of claim 4 wherein said block copolymer is a styrenic block copolymer.

6. The dental floss of claim 5 wherein the block copolymer is a selected from the group consisting of styrene-isoprene-styrene, styrene-butadiene-styrene, and styrene-ethylene-butylene-styrene copolymers.

7. The dental floss of claim 1 wherein said thermoplastic elastomer is a gelatinous thermoplastic elastomer.

8. The dental floss of claim 7 wherein said gelatinous thermoplastic elastomer is a gelatinous plasticized poly (styrene-ethylene-butylene-styrene) triblock copolymer.

9. The dental floss of claim 1 wherein the outer sheath has a Shore A hardness of 10 or less.

10. The dental floss of claim 1 wherein the coating level of the outer sheath is from 150 to 400% based on the denier of the fiber.

11. The dental floss of claim 1 wherein the outer sheath is applied by coating the fiber core with a solution comprising said thermoplastic elastomer.

12. The dental floss of claim 1 wherein the outer sheath is applied by coating the fiber core with a hot melt comprising said thermoplastic elastomer.

13. A method for making a dental floss comprising: (a) providing a multifilament fiber; and (b) applying a sheath layer including a thermoplastic elastomer and an extender selected from the group consisting of oils, resins, and asphalts, to the surface of the multifilament fiber to provide a dental floss.

14. The method of claim 13, further comprising bulking a portion of the multifilament fiber prior to step (b), to form brush portions.

15. The method of claim 13 wherein the thermoplastic elastomer comprises a block copolymer.

16. The method of claim 13 wherein said block copolymer is a styrenic block copolymer.

17. The method of claim 16 wherein the block copolymer is a selected from the group consisting of styrene-isoprene-styrene, styrene-butadiene-styrene, and styrene-ethylene-butylene-styrene copolymers.

18. The method of claim 13 wherein said applying step comprises coating the multifilament fiber with a solution comprising the thermoplastic elastomer.

19. The method of claim 13 wherein said applying step comprises coating the multifilament fiber with a hot melt comprising the thermoplastic elastomer.

20. The method of claim 13 wherein said applying step comprises wire coating the thermoplastic elastomer onto the multifilament fiber.

21. A method of flossing the teeth of a mammal by inserting between two teeth of the mammal a length of a dental floss comprising a fiber core and sheath comprising a thermoplastic elastomer and an extender selected from the group consisting of oils, resins, and asphalts.

22. The method of claim 21 wherein said fiber core comprises a multifilament fiber.

23. The method of claim 21 wherein said thermoplastic elastomer comprises a block copolymer.

24. The method of claim 21 wherein said sheath has a Shore A hardness of 10 or less.

25. A dental floss comprising a fiber core and an outer sheath comprising a thermoplastic elastomer, the outer sheath having a Shore A hardness of 10 or less.

26. The dental floss of claim 35 wherein the fiber core comprises a multifilament fiber.

27. The dental floss of claim 26, wherein the multifilament fiber includes a brush portion.

28. The dental floss of claim 25, wherein the thermoplastic elastomer comprises a block copolymer.

29. The dental floss of claim 28, wherein said block copolymer is a styrenic block copolymer.

30. The dental floss of claim 29, wherein the block copolymer is selected from the group consisting of styrene-isoprene-styrene, styrene-butadiene-styrene, and styrene-ethylene-butylene-styrene copolymers.

31. The dental floss of claim 29 wherein the outer sheath further comprises an extender.

32. The dental floss of claim 31 wherein the extender is selected from the group consisting of oils, waxes, resins and asphalts.

33. The dental floss of claim 25, wherein said thermoplastic elastomer is a gelatinous thermoplastic elastomer.

34. The dental floss of claim 33, wherein said gelatinous thermoplastic elastomer is a gelatinous plasticized poly-(styrene-ethylene-butylene-styrene) tri-block copolymer.

35. The dental floss of claim 25 wherein the outer sheath further comprises an extender.

36. The dental floss of claim 25, wherein the coating level of the outer sheath is from 150 to 400% based on the denier of the fiber.

37. The dental floss of claim 25, wherein the outer sheath is applied by coating the fiber core with a solution comprising said thermoplastic elastomer.

38. The dental floss of claim 25, wherein the outer sheath is applied by coating the fiber core with a hot melt comprising said thermoplastic elastomer.

39. A dental floss comprising a fiber core and an outer sheath comprising a thermoplastic elastomer, the coating level of the outer sheath being from 150 to 400% based on the denier of the fiber.

40. The dental floss of claim 39 wherein the fiber core comprises a multifilament fiber.

41. The dental floss of claim 39 wherein the multifilament fiber includes a brush portion.

42. The dental floss of claim 39 wherein the thermoplastic elastomer comprises a block copolymer.

43. The dental floss of claim 42 wherein said block copolymer is a styrenic block copolymer.

44. The dental floss of claim 43 wherein the block copolymer is selected from the group consisting of styreneisoprene-styrene, styrene-butadiene-styrene, and styrene-ethylene-butylene-styrene copolymers.

45. The dental floss of claim 43 wherein the outer sheath further comprises an extender.

46. The dental floss of claim 45 wherein the extender is selected from the group consisting of oils, waxes, resins and asphalts.

47. The dental floss of claim 39 wherein said thermoplastic elastomer is a gelatinous thermoplastic elastomer.

48. The dental floss of claim 47 wherein said gelatinous thermoplastic elastomer is a gelatinous plasticized poly-(styrene-ethylene-butylene-styrene) tri-block copolymer.

49. The dental floss of claim 39 wherein the outer sheath further comprises an extender.

50. The dental floss of claim 39 wherein the outer sheath is applied by coating the fiber core with a solution comprising said thermoplastic elastomer.

51. The dental floss of claim 39 wherein the outer sheath is applied by coating the fiber core with a hot melt comprising said thermoplastic elastomer.

52. A method of flossing the teeth of a mammal by inserting between two teeth of the mammal a length of a dental floss comprising a fiber core and a sheath comprising a thermoplastic elastomer, said sheath having a Shore A hardness of 10 or less.

53. A method of flossing the teeth of a mammal by inserting between two teeth of the mammal a length of a dental floss comprising a fiber core and a sheath comprising a thermoplastic elastomer, the coating level of the outer sheath being from 150 to 400% based on the denier of the fiber.

54. A method of making a dental floss comprising: (a) providing a multifilament fiber; and (b) applying a sheath layer including a thermoplastic elastomer to the surface of the multifilament fiber to provide a dental floss, said sheath layer having a Shore A hardness of 10 or less.

55. A method of making a dental floss comprising: (a) providing a multifilament fiber; and (b) applying a sheath layer including a thermoplastic elastomer to the surface of the multifilament fiber to provide a dental floss, the coating level of the outer sheath being from 150 to 400% based on the denier of the fiber.

56. A dental floss comprising a fiber core and an outer sheath comprising a thermoplastic elastomer comprising a styrene-isoprene block copolymer, the styrene:isoprene ratio being about 21:79.

* * * * *